United States Patent [19]

Clark et al.

[11] Patent Number: 5,192,770
[45] Date of Patent: Mar. 9, 1993

[54] SEROTONERGIC ALPHA-OXOACETAMIDES

[75] Inventors: Robin D. Clark, Palo Alto; Richard M. Eglen, Mountain View; Joseph M. Muchowski; William L. Smith, both of Sunnyvale; Klaus K. Weinhardt, San Francisco, all of Calif.

[73] Assignee: Syntex ( U.S.A.) Inc., Palo Alto, Calif.

[21] Appl. No.: 624,028

[22] Filed: Dec. 7, 1990

[51] Int. Cl.$^5$ .................... A61K 31/44; C07D 453/02
[52] U.S. Cl. .................................. 514/305; 514/205; 546/133; 540/552; 540/584
[58] Field of Search ................ 546/133; 540/552, 584; 514/305, 214

[56] References Cited

U.S. PATENT DOCUMENTS

| | | | |
|---|---|---|---|
| 4,146,628 | 3/1979 | Oppenheimer et al. | 514/305 |
| 4,822,795 | 4/1989 | King | 514/305 |
| 4,853,376 | 8/1989 | King | 514/305 |

FOREIGN PATENT DOCUMENTS

| | | | |
|---|---|---|---|
| 7696150 | 7/1971 | Belgium | 546/133 |
| 237281A | 9/1987 | European Pat. Off. | 546/133 |
| 311724A | 4/1989 | European Pat. Off. | 546/133 |
| WO90/14347 | 11/1990 | PCT Int'l Appl. | 546/133 |

OTHER PUBLICATIONS

Fozard, J. R., 5-HT: The Enigma Variations, *Trends Pharmacol. Sci.* 1987; 8: 501–506.
Drugs Acting on 5-Hydroxytryptamine Receptors, *The Lancet*, Sep. 23, 1989; pp. 717–719.
Reynolds, J. C., Prokinetic Agents: A Key in the Future of Gastroenterology, *Gastroenterology Clinics of North America*, 1989; 18: 437–457.
Peatfield, R., Drugs and the Treatment of Migraine, *Trends Pharmacol. Sci.* 1988; 9: 141–145.
King, F. D. et al., 5-HT$_3$ Receptor Antagonists, *Drugs of the Future*, 1989; 14: 875–889.
Turconi, M. et al., Synthesis of a New Class of 2,3-Dihydro-2-oxo-1H-Benzimidazole-1-Carboxylic Acid Derivatives as Highly Potent 5-HT$_3$ Receptor Antagonists, *J. Med. Chem.*, 1990; 33: 2101–2108.
Poletto, J. F. et al., Synthesis and Antiinflammatory Evaluation of Certain 5-Alkoxy-2,7-Dialkyltryptamines, *J. Med. Chem.*, 1973; 16(7): 757–765.
Nogrady et al., Indole Hydrazides as Potential Monoamine Oxidase Inhibitors, *J. Med. Chem.*, 1966; 9: 438–439.
Franke, A., Synthesis and Reactions of (o-Acylamino)-Phenylglyoxylic Amides, *Liebigs Ann. Chem.*, 1982; 4: 794–804.

*Primary Examiner*—Richard L. Raymond
*Assistant Examiner*—Shailendra Kumar
*Attorney, Agent, or Firm*—Wayne W. Montgomery; Derek P. Freyberg; Tom M. Moran

[57] ABSTRACT

α-Oxoacetamides of the formula $R^1C(O)C(O)NR^2R^3$ in which $R^1$ is optionally substituted phenyl, 1-indolyl, 2,3-dihydro-1-indolyl, 1-benzimidazolidinonyl, 3-benzofuranyl, 3-benzothiophenyl, 3-indolyl, and 1,2-alkano-3-indolyl; $R^2$ is selected from:

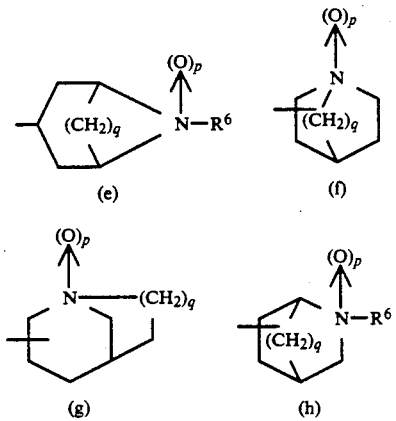

and $R^3$ is selected from hydrogen or lower alkyl; and the pharmaceutically acceptable salts, individual isomers, mixtures of isomers, processes for preparation, compositions, and methods of use thereof.

34 Claims, No Drawings

SEROTONERGIC ALPHA-OXOACETAMIDES

FIELD OF THE INVENTION

This invention relates to α-oxoacetamides which possess serotonergic receptor activity. The invention also relates to the pharmaceutical compositions containing such compounds and to the methods for their use and preparation.

BACKGROUND OF THE INVENTION

Serotonin, a neurotransmitter with mixed and complex pharmacological characteristics, was first discovered in 1948 and subsequently has been the subject of an immense quantity of research. Serotonin, also referred to as 5-hydroxytryptamine (5-HT), acts both centrally and peripherally on discrete 5-HT receptors. Current dogma delineates 5-HT receptors into three major sub-classifications—$5\text{-}HT_1$, $5\text{-}HT_2$ and $5\text{-}HT_3$—each of which may also be heterogeneous.

Molecules which selectively interact with the serotonergic receptor subtypes represent a family of drugs with a diversity of therapeutic applications. For example, $5\text{-}HT_1$ receptor agonists are clinically indicated for anxiety, hypertension and migraine. Selective $5\text{-}HT_2$ receptor antagonists are marketed as anxiolytics, antidepressants, anti-hypertensives and appetite stimulants (see 5-HT: The Enigma Variations. J. R. Fozard 1987; *Trends. Pharmacol. Sci.* 8: 501).

$5\text{-}HT_3$ receptor antagonists are known for their potent antiemetic properties, particularly against emesis induced by cancer chemotherapy and radiotherapy, and for their gastrokinetic activity (see respectively Drugs Acting on 5-Hydroxytryptamine Receptors: *The Lancet* Sep. 23, 1989 and references cited therein and Reynolds R. C. Prokinetic Agents: A Key in the Future of Gastroenterology. *Gastroenterology Clinics of North America* 1989; 18: 437–457). In addition, $5\text{-}HT_3$ receptor antagonists are under investigation for treating CNS diseases involving cognitive dysfunctions, anxiety, dependency disorders and schizophrenia (see article from *The Lancet* previously cited) and may also be of value in the control of pain, particularly migraine (see Peatfield R. 1988; Drugs and the Treatment of Migraine. *Trends, Pharmacol. Sci.* 9: 141).

The disclosures of these and other documents referred to throughout this application, e.g., in the Pharmacology section of the Detailed Description of the Invention, are incorporated herein by reference.

SUMMARY OF THE INVENTION

The first aspect of this invention is the compounds of Formula I:

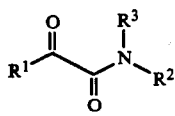
(I)

wherein R¹ is selected from

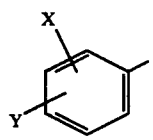
(a)

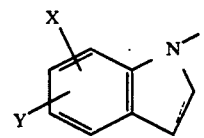
(b)

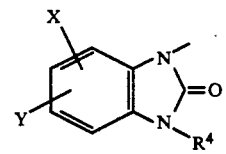
(c)

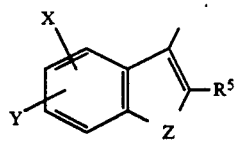
(d)

in which:
the dashed line denotes an optical bond;
X and Y are independently selected from hydrogen, halo, cyano, hydroxy, lower alkoxy, lower alkyl, nitro, amino, aminocarbonyl, (lower alkyl)amino, di(lower alkyl)amino, and (lower alkanoyl)amino;
Z is —O—, —S— or —N(R⁴)—; and
R⁴ and R⁵ are independently selected from hydrogen or lower alkyl or are together —(CH₂)ₙ— wherein n is an integer from 3 to 5;
R² is selected from

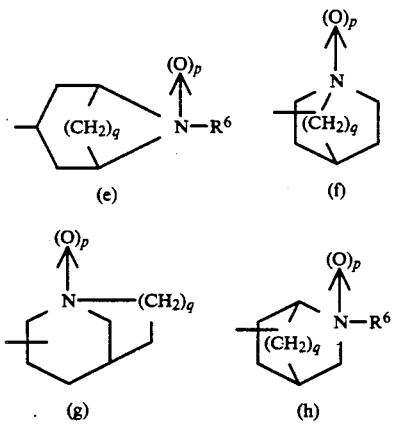

in which
p is 0 or 1;
q is 1, 2 or 3; and
R⁶ is $C_{1-7}$ alkyl, $C_{3-8}$ cycloalkyl, $C_{3-8}$ cycloalkyl-$C_{1-2}$ alkyl, or a group $(CH_2)_t R^7$ where t is 1 or 2 and R⁷ is thienyl, pyrrolyl, or furyl, each optionally further substituted by one or two substituents selected from $C_{1-6}$ alkyl, $C_{1-6}$ alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally substituted by hydroxy, $C_{1-4}$ alkoxy, carboxy, esterified carboxy or in vivo hydrolyzable acyloxy; and R³ is selected from hydrogen or lower alkyl; or their pharmaceutically acceptable salts, individual isomers and mixtures of isomers.

A second aspect of this invention is pharmaceutical compositions containing a compound of Formula I in admixture with one or more suitable excipients.

A third aspect of this invention is methods for treating diseases involving emesis, gastrointestinal disorders, CNS disorders, cardiovascular disorders or pain by administering a therapeutically effective amount of a compound of Formula I to a subject in need thereof.

A fourth aspect of this invention is a process for preparing compounds of Formula I and is set forth in the "Detailed Description Of The Invention."

DETAILED DESCRIPTION OF THE INVENTION

Definitions

Unless otherwise stated, the following terms used in the specification and claims have the meanings given below:

"Active ingredient" means a pharmaceutically effective amount, as defined above, of a compound of Formula I.

"Alkyl" means a straight, branched, or cyclic saturated hydrocarbon radical having from one to the number of carbon atoms designated. For example $C_{1-7}$ alkyl is alkyl having at least one but no more than seven carbon atoms, e.g., methyl, ethyl, i-propyl, n-propyl, n-butyl, cyclopropylmethyl, pentyl, cyclohexyl, heptyl and the like.

"Animal" includes humans, non-human mammals (such as dogs, cats, rabbits, cattle, horses, sheep, goats, swine, and deer) and non-mammals such as birds and the like.

"Carboxy" means the carboxyl group —COOH.

"Cytotoxic agents" include platinum anti-cancer agents such as cisplatin (cis-diamminedichloroplatinum), as well as non-platinum anti-cancer drugs such as cyclophosphamide (cytoxin), vincristrine (leurocristine), procarbazine (N-(1-methylethyl)-4-[(2-methylhydrazino)methyl]benzamide), methotrexate, fluorouracil, mechlorethamine hydrochloride (2-chloro-N-(2-chloroethyl)-N-methylethanamine hydrochloride), doxorubicin, adriamycin, dactinomycin (actinomycin-D) cytarabine, carmustine, dacarbazine, and others listed at page 1143 of the *Journal of Clinical Oncology* 1989; 7(8): 1143.

"Disease" specifically includes any unhealthy condition of an animal or part thereof and may be caused by, or incident to, medical or veterinary therapy applied to that animal, i.e., the "side effects" of such therapy. Thus, "disease" here includes the emesis caused by therapy with agents having emetogenic side effects, in particular by therapy for cancer, such as chemotherapy with cytotoxic agents and radiotherapy.

"Emesis", for the purposes of this application, will have a meaning that is broader than the normal, dictionary definition and includes not only vomiting, but also nausea and retching.

"Esterified carboxy" means the ester group —COOR wherein R is alkyl as defined above.

"Halogen" means fluorine, chlorine, bromine, or iodine. Preferred halogens are chlorine and fluorine;

"In vivo hydrolyzable acyloxy" means a group —OC(O)R, wherein R is alkyl as defined above, capable of undergoing enzymatic hydrolysis within a living organism.

"Leaving group" has the meaning conventionally associated with it in synthetic organic chemistry, i.e., an atom or group displaceable under alkylating conditions, and includes halogen, mesyloxy, benzenesulfonyloxy, alkane- or arenesulfonyloxy such as ethanesulfonyloxy, tosyloxy and the like "Lower alkyl" means an alkyl of one to six carbon atoms, i.e., $C_{1-6}$ alkyl.

"Lower alkoxy", "(lower alkyl)amino", "di(lower alkyl)amino", "(lower alkanoyl)amino", and similar terms mean alkoxy, alkylamino, dialkylamino, alkanoylamino, etc. in which the or each alkyl or alkanoyl radical contains from one to six carbon atoms.

"Optional" or "optionally" means that the subsequently described event or circumstance may or may not occur, and that the description includes instances where the event or circumstance occurs and instances in which it does not. For example, "optional bond" means that the bond may or may not be present and that the description includes both single bonds and double bonds; "Optionally followed by converting the free base to the acid addition salt" means that the conversion may or may not be carried out in order for the process described to fall within the invention, and the invention includes those processes wherein the free base is converted to the acid addition salt and those processes in which it is not.

"Pharmaceutically acceptable" means that which is useful in preparing a pharmaceutical composition that is generally safe and non-toxic and includes that which is acceptable for veterinary use as well as human pharmaceutical use.

"Pharmaceutically acceptable salts" means salts which possess the desired pharmacological activity and which are neither biologically nor otherwise undesirable. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclooct-2-[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed wherein hydroxy substituents present are capable of forming salts with inorganic or organic bases. Acceptable inorganic bases include sodium hydroxide, sodium carbonate, potassium hydroxide, aluminum hydroxide and calcium hydroxide. Acceptable organic bases include diethanolamine, tromethamine, N-methylglucamine, ethanolamine, triethanolamine, and the like.

"Pharmaceutically effective amount" means that amount which, when administered to an animal for treating a disease, is sufficient to effect such treatment, as defined above, for the disease.

"Treatment" means any treatment of a disease in an animal and includes:

(1) preventing the disease from occurring in an animal which may be predisposed to the disease but does not yet experience or display symptoms of the disease,
(2) inhibiting the disease, i.e., arresting its development, or
(3) relieving the disease, i.e., causing regression of the disease.

Compounds that have identical molecular formulae but differ in the nature or sequence of bonding of their atoms or in the arrangement of their atoms in space are termed "isomers". Isomers that differ in the nature or sequence of bonding of their atoms are termed "constitutional isomers". Isomers that differ only in the arrangement of their atoms in space are termed "stereoisomers". Stereoisomers that are not mirror images of one another are termed "diasteromers" and stereoisomers that are mirror images are termed "enantiomers" or sometimes "optical isomers". Stereoisomers that are superimposable upon their mirror images are termed "achiral" and those not superimposable are termed "chiral". A carbon atom bonded to four different groups is termed a "chiral center" or alternatively an "asymmetric carbon".

When a compound has a chiral center, a pair of enantiomers of opposite chirality is possible. An enantiomer may be characterized by the absolute configuration of its chiral center and described by the R- and S-sequencing rules of Cahn and Prelog (i.e., as (R)- and (S)-isomers) or by the manner in which the molecule rotates the plane of polarized light and designated as dextrorotatory or levorotatory (i.e., as (+)- and (−)-isomers, respectively). A compound may exist as either individual enantiomer or as a mixture thereof. A mixture containing equal proportions of the enantiomers is termed a "racemic mixture" or "racemate" and may be described as the (RS)- or (±)-mixture thereof. Unless indicated otherwise, the description or naming of a particular compound in the specification and claims is intended to include both individual enantiomers and mixtures, racemic or otherwise, thereof. Conventions for stereochemical nomenclature, methods for the determination of sterochemistry and the separation of stereoisomers are well-known in the art (see discussion in Chapter 4 of "Advanced Organic Chemistry", 3rd edition, March, Jerry, John Wiley and Sons, New York, 1985).

Certain compounds of Formula I may exist as stereoisomers. For example, the $R^2$ substituent described herein may exhibit a chiral center at the ring carbon which is bonded to the α-oxoacetamide nitrogen. In addition, compounds of Formula I may exist as the endo or exo form, e.g., when the $R^2$ substituent is 1-azabicyclo[3.3.1]non-4-yl.

When a compound of Formula I exhibits a chiral center, a pair of enantiomers exists. When a compound of Formula I exhibits a chiral center and may exist as endo or exo, four separate stereoisomers are possible, i.e., a pair of enantiomers in the endo or exo form.

It is to be understood that when referring to Formula I or subformulae (f), (g) and (h) in this application, a straight line depicting the covalent bond between the asymmetric carbon and the amide nitrogen represents either the R or S configuration or a mixture, racemic or otherwise, thereof. For purposes of the present application when referring to a compound by name or by formula and endo or exo is not designated, it is to be understood that the reference is to both forms.

Certain $R^2$ substituents described in this application are of particular interest and are therefore defined specifically. These $R^2$ substituents of particular interest are as follows:

(1) subformula (f) where q is 2 and p is 0 having the specific formula

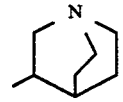

is referred to as 1-azabicyclo[2.2.2]oct-3-yl;

(2) subformula (f) where q is 2 and p is 0 having the specific formula

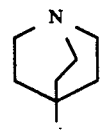

is referred to as 1-azabicyclo[2.2.2]oct-4-yl;

(3) subformula (e) where q is 3, p is 0 and $R^6$ is methyl having the specific formula

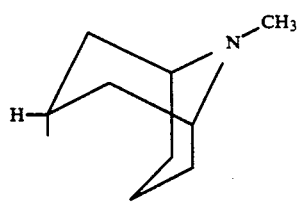

is referred to as endo-9-methyl-9-azabicyclo[3.3.1]-non-3-yl;

(4) subformula (e) where q is 3, p is 0 and $R^6$ is methyl having the specific formula

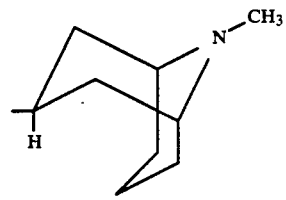

is referred to as exo-9-methyl-9-azabicyclo[3.3.1]-non-3-yl;

(5) subformula (e) where q is 2, p is 0 and $R^6$ is methyl having the specific formula

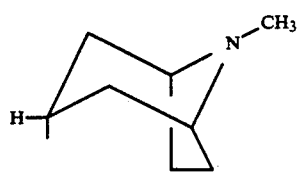

is referred to as endo-8-methyl-8-azabicyclo[3.2.1]oct-3-yl;

(6) subformula (e) where q is 2, p is 0 and $R^6$ is methyl having the specific formula

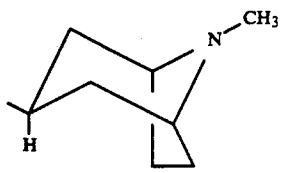

is referred to as exo-8-methyl-8-azabicyclo[3.2.-1]oct-3-yl;

(7) subformula (g) wherein q is 2 and p is 0 having the specific formula

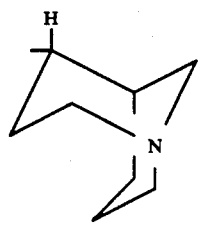

is referred to as endo-1-azabicyclo[3.3.1]non-4-yl; and (8) subformula (g) wherein q is 2 and p is 0 having the specific formula

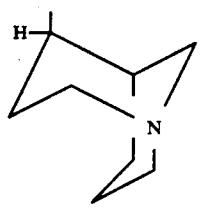

is referred to as exo-1-azabicyclo[3.3.1]non-4-yl.

Compounds of Formula I are named in accordance with generally acceptable nomenclature rules established by "Chemical Abstracts". For example, the compound of Formula I

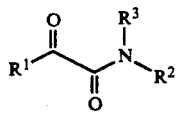

wherein $R^2$ is 1-azabicyclo[2.2.2.]oct-3-yl and $R^3$ is hydrogen is named

N-(1-azabicyclo[2.2.2]oct-3-yl)-α-oxo-benzeneacetamide when $R^1$ is Formula (a) and X and Y are each hydrogen;

N-(1-azabicyclo[2.2.2]oct-3-yl)-α-oxo-1-indoleacetamide when $R^1$ is Formula (b), the double bond is present and X and Y are each hydrogen;

N-(1-azabicyclo[2.2.2]oct-3-yl)-α-oxo-1-benzimidazolidinoneacetamide when $R^1$ is Formula (c) and X, Y and $R^4$ are each hydrogen;

N-(1-azabicyclo[2.2.2]oct-3-yl)-α-oxo-3-benzothiopheneacetamide when $R^1$ is Formula (d), Z is —S— and X, Y and $R^5$ each hydrogen;

N-(1-azabicyclo[2.2.2]oct-3-yl)-α-oxo-3-benzofuranacetamide when $R^1$ is Formula (d), Z is —O— and X, Y and $R^5$ are each hydrogen;

N-(1-azabicyclo[2.2.2]oct-3-yl)-α-oxo-3-indoleacetamide when $R^1$ is Formula (d), Z is —NH— and and X, Y and $R^5$ are each hydrogen; and N-(1-azabicyclo[2.2.2]oct-3-yl)-1,2,3,4-tetrahydro-α-oxo-10-pyrido[1,2-a]indoleacetamide when $R^1$ is Formula (d), Z is —N($R^4$)—, $R^4$ and $R^5$ together are —(CH$_2$)$_4$— and X and Y are each hydrogen.

Utility

Compounds of Formula I exhibit utility in treating a broad range of diseases in animals, particularly humans. Examples of diseases that may be treated using the compounds of Formula I include emesis, gastrointestinal disorders, cardiovascular disorders, pain and central nervous system (CNS) disorders, particularly anxiety.

Compounds of Formula I may be useful in the prevention and treatment of emesis. Causes of such emesis include surgical anesthesia, psychological stress, pregnancy, certain disease states, radiotherapy, radiation poisoning and toxic substances. Disease states which are known to induce emesis include conditions such as gut obstruction, raised intracranial pressure, acute myocardial infarction, migraine headaches and adrenal crisis. Toxic substances which induce emesis include toxins in the form of abnormal metabolites or abnormal accumulation of natural occurring substances associated with such conditions as hepatic coma, renal failure, diabetic ketoacidosis, hyperthyroid crisis, both hypo- and hyperparathyroidism and Addison's disease. Emesis may also be caused by ingested toxins, e.g., enterotoxins in staphylococcus-contaminated foods, or by drugs administered for therapeutic purposes, e.g., digitalis, emetine, histamine and chemotherapeutic agents.

Compounds of Formula I may be of particular value in treating (especially preventing) the emesis induced by radiation poisoning, treatment for cancer with radiotherapy or chemotherapy with cytotoxic agents or drug therapy in general wherein a treatment-limiting side effect is emesis, e.g., amphotericin B in treating immunosuppressed patients, zidovidine (AZT) in the treatment of AIDS and interleukin in treating cancer.

Compounds of Formula I possess prokinetic activity and may be useful in the treatment of gastrointestinal diseases, i.e., diseases of the stomach, esophagus and of both the large and small intestines. Examples of specific diseases include, but are not limited to, dyspepsia (e.g., non-ulcer dyspepsia), gastric stasis, peptic ulcer, reflux esophagitis, flatulence, bile reflux gastritis, pseudo-obstruction syndrome, irritable colon syndrome (which may result in chronic constipation and diarrhea), diverticular disease, biliary dysmotility (which may result in sphincter of Oddi dysfunction and "sludge" or microscopic crystals in the gall bladder), gastroparesis (e.g., diabetic, postsurgical or idiopathic), irritable bowel syndrome amd retarded gastric emptying. The compounds of Formula I are also useful as short-term prokinetics to facilitate diagnostic radiology and intestinal intubation. In addition, the compounds are useful for treating diarrhea, particularly diarrhea induced by cholera and carcinoid syndrome.

Compounds of Formula I are active in models of anxiety, cognition deficit and drug withdrawal and may be useful in treating diseases of the central nervous system. Categories of such diseases include cognitive disorders, psychoses, obsessive/compulsive and anxiety/depression behavior. Cognitive disorders include attentional or memory deficit, dementia states (including senile dementia of the Alzheimer's type and aging), cerebral vascular deficiency and Parkinson's disease. Psychoses that may be treated using the compounds of this invention include paranoia, schizophrenia and autism. Representative, treatable anxiety/depressive states include anticipatory anxiety (e.g., prior to surgery, dental work, etc.), depression, mania, convulsions and anxiety caused by withdrawal from addictive substances such as opiates, benzodiazapines nicotine, alcohol, cocaine and other drugs of abuse.

Compounds of Formula I may be useful in the treatment of cardiovascular diseases. Such diseases may include arrhythmias and hypertension.

It is thought that 5-$HT_3$ antagonists prevent certain adverse nervous transmissions and/or prevent vasodilation and are therefore of value for reducing perceived levels of pain. Compounds of Formula I are, therefore, useful in treating pain such as that associated with cluster headaches, migraines, trigeminal neuralgia and visceral pain (e.g., that caused by abnormal distension of hollow visceral organs).

In summary, an aspect of this invention is a method for treating an animal, particularly a human, exhibiting a disease involving emesis, a gastrointestinal disorder, a cardiovascular disorder, pain or a CNS disorder, particularly anxiety, comprised of administering a therapeutically effective amount of a compound of Formula I to such animal.

Pharmacology

5-$HT_3$ receptor binding affinity may be determined by the Rat Cerebral Cortex Binding Assay, a predictive in vitro assay which assesses the binding affinity of a compound for the 5-$HT_3$ receptor. See methods described in Kilpatrick, G. J., Jones, B. J. and Tyers, M. B., *Nature* 1987; 330: 24–31. The assay, as adapted for testing compounds of Formula I, is set out in Example 7 of this application. The compounds of Formula I exhibit affinity for the 5-$HT_3$ receptor in this assay.

5-$HT_3$ receptor antagonist activity may be determined by measuring inhibition of the von Bezold-Jarisch reflex in anesthetized rats, an accepted in vivo assay for 5-$HT_3$ receptor antagonist activity. See methods of Butler, A., Hill, J. M., Ireland, S. J., Jordan, C. C., Tylers, M. B., *Brit. J. Pharmacol.* 1988; 94: 397–412; Cohen, M. L., Bloomquist, W., Gidda, J. S., Lacefield, W., *J. Pharmacol. Exp. Ther.* 1989; 248: 197–201; and Fozard, J. R., MDL 72222: *Arch. Pharmacol.* 1984; 326: 36–44. The details of the procedure, as modified for testing the compounds Formula I, are set out in Example 8 of this application. Compounds of Formula I inhibit the von Bezold-Jarisch reflex.

Anti-emetic activity may be determined by measuring reduction of cisplatin-induced emesis in ferrets, an accepted in vivo test for determining anti-emetic activity. See methods by Costall, B., Domeney, A. M., Naylor, R. J., and Tattersall, F. D., *Neuropharmacology* 1986; 25(8): 959–961; and Miner, W. D. and Sanger G. J., *Brit. J. Pharmacol.* 1986; 88: 497–499. A general description is set out in Example 9 of this application. Compounds of Formula I exhibit anti-emetic activity in this assay.

Anti-emetic activity may also be determined by measuring reduction of cisplatin-induced emesis in dogs. See methods described by Smith, W. L., Alphin, R. S., Jackson, C. B., J. Pharm., and Sancilio, *J. Pharm. Pharmacol.* 1989; 41: 101–105; and Gylys, J. A., *Res. Commun. Chem. Pathol. Pharmacol.* 1979; 23(1): 61–68. A more detailed description, as modified for testing the Compounds of Formula I, is set out in Example 10 of this application. Compounds of Formula I exhibit anti-emetic activity in this assay.

Prokinetic activity may be determined by measuring the rate of gastric emptying after oral administration of test meal to rats. See methods developed by Droppleman, D., Gregory, R., and Alphin, R. S., *J. Pharmacol. Methods* 1980; 4(3): 227–30. The procedures of Droppleman et al. are accepted methods for determining prokineteic activity in vivo. The prokinetic assay is detailed in Example 11 of this application. Compounds of Formula I exhibit prokinetic activity in this assay.

Anxiolytic activity is determined by the art-recognized Crawley and Goodwin two-compartment exploratory model as described in Kilfoil, T., Michel, A., Montgomery, D., and Whiting, R. L., *Neuropharmacology* 1989; 28(9): 901–905. In brief, the method involves determining whether a compound reduces the natural anxiety of mice in a novel, brightly lighted area. A detailed description is set forth in Example 12 of this application. Compounds of Formula I exhibit anxiolytic activity in this assay.

Cognition enhancing activity may be determined by the mouse habituation/cognitive enhancement test. See procedures described in Barnes, J. M., Costall, B., Kelly, M. E., Naylor, F. J., Onaivi, E. S., Tomkins, D. M. and Tyers, M. B. *Br. J. Pharmacol.* 1989; 98: 693P. This procedure utilizes the exploratory model described above to test for improvements in the impaired cognitive performance of aged mice. A detailed description is set forth in Example 13 of this application. Compounds of Formula I exhibit cognition enhancing activity in this assay.

Anxiolytic activity during withdrawal from drugs of abuse may be determined by the mouse light/dark withdrawal anxiety test. See methods described in Carboni, E., Acquas, E., Leone, P., Perezzani, L., and Di Chiara, G., *Eur. J. Pharmacol* 1988; 151: 159–160. This procedure utilizes the exploratory model described above to test for anxiolytic activity after chronic administration and subsequent abrupt cessation of alcohol, cocaine or nicotine treatments. A detailed description is set forth in Example 14 of this application. Compounds of Formula I exhibit activity at reversing the drug withdrawal-induced anxiety in this assay.

Administration and Pharmaceutical Composition

In general, compounds of Formula I will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. Therapeutically effective amounts of compounds of Formula I may range from aproximately 1.0 nanogram per Kg (ng/Kg) body weight per day to 1.0 mg/Kg body weight per day. Preferably the amount will be approximately 10 ng/Kg/day to 0.1 mg/Kg/day. Therefore, a therapeutically effective amount for a 70 Kg human may range from 70 ng/day to 70 mg/day, preferably 700 ng/day to 7.0 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

Generally compounds of Formula I will be administered as Pharmaceutical compositions either orally, systemically (e.g., transdermally, intranasally or by suppository) or parenterally (e.g., intramuscularly, intravenously or subcutaneously). Compositions can take the form of tablets, pills, capsules, semisolids, powders, sustained release formulations, solutions, suspensions, elixirs, aerosols, or any other appropriate composition and are, in general, comprised of the active ingredient in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the active ingredient in aerosol form. Inert gases suitable for this purpose are nitrogen, carbon dioxide, nitrous oxide, etc. Other suitable pharmaceutical carriers and their formulations are described in A. R. Alfonso 1985. *Remington's Pharmaceutical Sciences*. 17th ed. Easton, Pa.: Mack Publishing Company.

The amount of a compound of Formula I in the composition may vary widely depending upon the type of formulation, size of a unit dosage, kind of excipients and other factors known to those of skill in the art of pharmaceutical sciences. In general, the final composition will comprise about 0.000001% w to about 10.0% w of active ingredient with the remainder being the excipient or excipients. Preferably the level of active ingredient will be about 0.00001% w to about 1.0% w, with the remainder being a suitable excipient or excipients.

Preferably the pharmaceutical composition is administered in a single unit dosage form for continuous treatment or in a single unit dosage form ad libitum when relief of symptoms is specifically required.

Presently Preferred Embodiments

While the broadest definition of this invention is as set forth in the Summary of the Invention, certain embodiments are preferred. For example, preferred compounds of Formula I are those in which $R^3$ is hydrogen and the X and Y substituents of $R^1$ are independently selected from hydrogen or hydroxy.

Of particular interest are those compounds of Formula I in which $R^3$ is hydrogen, $R^2$ is 1-azabicyclo[2.2.2]oct-3-yl or 1-azabicyclo[2.2.2]oct-4-yl and $R^1$ is Formula (d).

Of most interest are those compounds of Formula I in which $R^3$ is hydrogen, $R^2$ is 1-azabicyclo[2.2.2]oct-3-yl and $R^1$ is Formula (d) wherein X and Y are hydrogen, Z is —N($R^4$)— and $R^4$ and $R^5$ are hydrogen or methyl or together are —(CH$_2$)$_n$—. Representative compounds are made by following the procedures set out in Examples 2, 3 and 4 of this application.

It is understood that these subgroups of special interest are particularly useful in the pharmaceutical compositions and methods of treatment of this invention.

Processes for Preparing Compounds of the Invention

Compounds of Formula I may be prepared by one of the reaction sequences shown below Scheme I

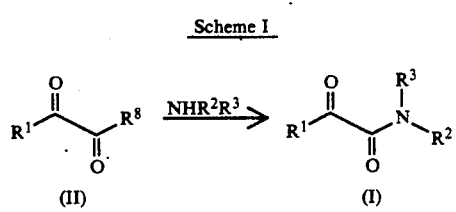

Scheme II

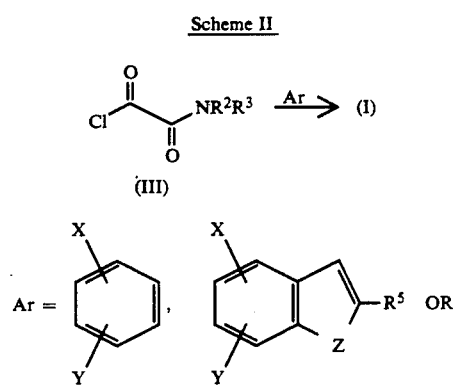

Scheme III

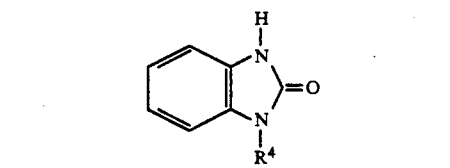

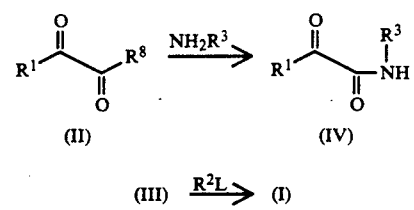

wherein each of X, Y, Z, $R^1$, $R^2$ and $R^3$ have their broadest definitions set forth in the Summary of the Invention, $R^8$ is halogen, hydroxy or alkoxy and L is a leaving group, with the processes applying particularly well to the presently preferred embodiments.

Scheme I

In a preferred method of synthesis, compounds of Formula I are prepared by reacting an α-oxoacetic acid derivative of Formula II, in which $R^8$ is halogen, with an appropriate substituted amine of the formula NHR$^2$R$^3$ (see Scheme I above). The reactants are stirred in a suitable organic solvent for 0.5 to 24 hours under ambient pressure and at a reaction temperature of −50° C. to 50° C.

Reactions may be carried out using either the free base or acid salt form of the substituted amine. When using the acid salt form the reaction must take place in the presence of base (e.g., an alkali hydroxide or alkali carbonate) preferably in a two phase solvent system consisting of water and a suitable organic solvent. Suitable organic solvents for reactions utilizing either the free base or acid salt form of the substituted amine include methylene chloride, toluene, ethyl acetate or ethers. Detailed descriptions of the above procedure are set forth in Examples 2 and 3 of this application.

Alternatively, Scheme I may be carried out by reacting an α-oxoacetic acid derivative of Formula II, in which $R^8$ is hydroxy or alkoxy, with an appropriate substituted amine of the formula $NHR^2R^3$. When $R^8$ is hydroxy the reaction conditions include the use of a dehydrating agent such as dicyclohexylcarbodiimide (DCC) or 1-hydroxybenzotriazole (HBOT). When $R^8$ is alkoxy the reaction may be carried out by heating the alkyl α-oxoacetate in the presence of the amine with or without solvent.

In general, the starting materials utilized in synthesizing compounds of Formula I are known to those of ordinary skill in the art. For example, the compound of Formula II in which $R^8$ is Cl and $R^1$ is Formula (d) wherein Z is —$NCH_3$— and each of $R^5$, X and Y is H, namely α-oxo-3-indoleacetyl chloride, is prepared by reacting N-methylindole with α-chloro-α-oxoacetyl chloride (1:1–1:3 mole ratio) in a suitable inert solvent, preferably one in which both reagents are soluble. The mixture is stirred for 0.5 to 24 hours under ambient pressure and at a reaction temperature of $-50°$ C. to $50°$ C., preferably $0°$ C. to $25°$ C. Suitable solvents include ethers, halogenated hydrocarbons, toluene and the like.

When the reaction between the indole and α-chloro-α-oxoacetyl chloride is carried out in an ether solvent (e.g., diethyl ether), the product may be insoluble and precipitate as a crystalline solid. Collection of this precipitate on a filter serves to purify the product from unreacted starting materials or any soluble by-product formed in the reaction. A more detailed description of this procedure is set forth in Example 1 of this application.

α-Oxo-3-benzothiopheneacetyl chloride, may be prepared by proceeding as above but replacing N-methylindole with benzothiophene. α-Oxo-3-benzofuranacetyl chloride, may be prepared by proceeding as above but replacing N-methylindole with benzofuran. The compound of Formula II in which $R^8$ is Cl and $R^1$ is Formula (d) wherein each X and Y is H, Z is —$NR^4$— and $R^4$ and $R^5$ are together —$(CH_2)_4$—, namely 1,2,3,4-tetrahydro-α-oxo-10-pyrido[1,2-a]indoleacetyl chloride, may be prepared by proceeding as above but replacing N-methylindole with 1,2,3,4-tetrahydropyrido[1,2-a]indole. 1,2,3,4-Tetrahydropyrido[1,2-a]indole may be prepared via an intramolecular Wittig reaction (M. D. Crenshaw and H. Zimmer, *J. Heterocyclic Chem.*, (1984) 21, 623).

Compounds of Formula II in which $R^8$ is Cl and $R^1$ is Formula (b) or (c) may be prepared by reacting an optionally substituted 1H-indole or N-alkylbenzimidazolidinone, respectively, with α-chloro-α-oxoacetyl chloride in the presence of a strong base such as sodium hydride.

The compound of Formula II in which $R^8$ is Cl and $R^1$ is Formula (a) wherein each of X and Y is H, namely α-oxo-benzeneacetyl chloride, may be prepared from α-oxo-benzeneacetic acid.

Compounds of Formula II in which $R^8$ is hydroxy or alkoxy may be prepared from the corresponding α-oxoacetyl chloride.

Compounds of Formula I in which $R^1$ is Formula (b) wherein the optional bond is absent may be prepared by reduction of the corresponding compound wherein the optional bond is present. The reduction is carried out under standard hydrogenation conditions with an appropriate hydrogenation catalyst and in a suitable polar, organic solvent. Reaction pressures may vary from atmospheric to approximately 15 megapascals (mPa) and temperatures may range from ambient to approximately $100°$ C. While any standard catalyst (e.g., rhodium on alumina, etc.) may be used, certain catalysts are favored. Preferred catalysts include 10% palladium hydroxide, 20% palladium hydroxide on carbon, Pearlman's catalyst (50% $H_2O$–20% palladium content) and palladium/$BaSO_4$. Suitable solvents include ethanol, DMF, acetic acid, ethyl acetate, tetrahydrofuran, toluene, and the like.

Depending upon the catalyst, solvent, pressure and temperature chosen, the reduction process may take from a few hours to a few days to complete. As an example, a reaction carried out with 20% palladium hydroxide in acetic acid and 70% perchloric acid at 15 kPa and $85°$ C. takes approximately 24 hours for full reduction to occur.

Scheme II

Alternatively, compounds of Formula I may be prepared by reacting an α-chloro-α-oxoacetamide of Formula III with optionally substituted benzene, indole, benzothiophene, benzofuran or N-alkylbenzimidazolidinone.

Compounds of Formula I in which $R^1$ is Formula (a) may be prepared by reacting a compound of Formula III with optionally substituted benzene in the presence of a Lewis acid such as aluminum chloride, boron trifluoride, hydrogen fluoride or phosphoric acid.

Compounds of Formula I in which $R^1$ is Formula (b) or (c) may be prepared by reacting a compound of Formula III with optionally substituted 1H-indole or N-alkylbenzimidazolidinone, respectively, in the presence of sodium hydride.

Compounds of Formula I in which $R^1$ is Formula (d) may be prepared by reacting a compound of Formula III with an optionally substituted 1H-indole, N-alkylindole, benzothiophene or benzofuran in a suitable inert solvent, preferably one in which both reagents are soluble. Suitable solvents include ethers, halogenated hydrocarbons, toluene and the like.

Compounds of Formula III may be prepared by proceeding as in Scheme I but replacing the α-oxoacetic acid derivative of Formula II with α-chloro-α-oxoacetyl chloride.

Substituted amines of the formula $NHR^2R^3$ that are particularly useful in the syntheses described in Schemes I and II are those wherein $R^2$ is one of the following radicals:
  1-azabicyclo[2.2.2]oct-3-yl;
  1-azabicyclo[2.2.2]oct-4-yl;
  endo-9-methyl-9-azabicyclo[3.3.1]non-3-yl;
  exo-9-methyl-9-azabicyclo[3.3.1]non-3-yl;
  endo-8-methyl-8-azabicyclo[3.2.1]oct-3-yl;
  exo-8-methyl-8-azabicyclo[3.2.1]oct-3-yl;
  endo-1-azabicyclo[3.3.1]non-4-yl; or
  exo-1-azabicyclo[3.3.1]non-4-yl;

Scheme III

Alternatively, compounds of Formula I may be prepared by a two step synthesis comprising (1) converting an α-oxoacetic acid derivative of Formula II to the corresponding unsubstituted or N-substituted α-oxoacetamide of Formula IV, followed by (2) condensation with an appropriate alkylating agent to form a compound of Formula I (see Scheme III above).

Step 1

Compounds of Formula IV may be prepared by proceeding as in Scheme I but replacing the substituted amine of the formula $NHR^2R^3$ with one of the formula $NH_2R^3$ wherein $R^3$ is hydrogen or lower alkyl.

Step 2

Compounds of Formula I may be prepared by reacting, in the presence of a strong base, a compound of Formula IV with an alkylating agent of the formula $R^2L$ wherein $R^2$ is defined as in its broadest definition set forth in the Summary of the Invention and L is a leaving group. The reaction is carried out under standard amide alkylating conditions (Luh, T. and Fung S. H., Synth. Commun. (1979), 9, 757) in an inert solvent at a reaction temperature of 20° C. to 100° C. Appropriate bases include sodium or sodium hydride and are usually employed in molar excess. Suitable solvents include N,N-dialkylformamides such as N,N-dimethylformamide or tetrahydrofuran.

Alternatively, alkylation may be accomplished via phase-transfer catalyst (PTC) techniques. Such techniques comprise carrying out the reaction in the presence of catalyst and in a liquid-liquid two phase solvent system (Gajda, T. and Zwierzak, A., Synthesis, Communications (1981), 1005), or preferably, in a solid-liquid system (Yamawaki, J., Ando, T. and Hanafusa, T., Chem, Lett. (1981), 1143; Koziara, A., Zawaszki, S. and Zwierzak, A., Synthesis (1979) 527, 549).

A liquid-liquid two-phase system is comprised of an aqueous phase consisting of a concentrated alkali hydroxide solution (e.g., 50% aqueous sodium hydroxide), a nonpolar phase comprised of an inert solvent, and an appropriate catalyst. A solid-liquid system consists of a powdered alkali hydroxide/alkali carbonate suspended in a nonpolar inert solvent and catalyst.

The reaction is effected by adding slowly to a PTC system containing a compound of Formula IV an alkylating agent of the formula $R^2L$ until 10 to 50% in excess. The reaction mixture is kept at reflux until the reaction is complete. The mixture is then cooled to room temperature and the compound of Formula I is isolated by conventional methods. Suitable nonpolar solvents include benzene, toluene, and the like. Appropriate catalysts include tetra-n-butyl-ammonium hydrogen sulfate, alumina coated with potassium fluoride, and tricaprylylmethylammonium chloride.

A variation of Scheme III comprises introducing the R substituent by methods described in Scheme III, Step 2 either prior to or after introduction of the $R^2$ substituent. That is, alkylating a compound of Formula IV or I, wherein $R^3$ is hydrogen, with an alkylating agent of the formula $R^3L$, wherein $R^3$ is lower alkyl and L is as defined above, to form a compound of Formula IV or I, respectively, wherein $R^3$ is lower alkyl.

Alkylating agents of the formula $R^2L$ that are particularly useful in this step are those wherein $R^2$ is one of the following radicals:

1-azabicyclo[2.2.2]oct-3-yl;
1-azabicyclo[2.2.2]oct-4-yl;
endo-9-methyl-9-azabicyclo[3.3.1]non-3-yl;
exo-9-methyl-9-azabicyclo[3.3.1]non-3-yl;
endo-8-methyl-8-azabicyclo[3.2.1]oct-3-yl;
exo-8-methyl-8-azabicyclo[3.2.1]oct-3-yl;
endo-1-azabicyclo[3.3.1]non-4-yl; or
exo-1-azabicyclo[3.3.1]non-4-yl

Additional Processes

Compounds of Formula I wherein substituents X and/or Y are $NH_2$ may be prepared by the reduction of a corresponding nitro substituent; wherein X and/or Y are alkoxy or dialkylamino, by substitution of a corresponding nitro or halo substituent; or wherein X and/or Y is hydroxy, by the de-alkylation of a corresponding alkoxy substituent. Furthermore, compounds of Formula I wherein Y is Cl, Br, I or $NO_2$ may be prepared by the introduction of such substituent onto a ring activated by a X substituent such as $NH_2$, NR, OH or alkoxy; or wherein X and/or Y is an acetamido substituent, by the acylation of a corresponding amino substituent. All of the additional processes described above may be preformed by methods well known to one of ordinary skill in the art of organic synthesis. Detailed descriptions of the preparation of a compounds of Formula I wherein X is hydroxy are set forth in Examples 4 and 5 of this application.

Compounds of Formula I wherein p is 1 (compounds of Formula I wherein the cyclic amine portion of $R^2$ is in the N-oxide form) may be prepared by oxidation of the corresponding compound of Formula I wherein p is 0, preferably the free base form. The oxidation is carried out at a reaction temperature of approximately 0° C. with an appropriate oxidizing agent and in a suitable inert, organic solvent. Suitable oxidizing agents include trifluoroperacetic acid, permaleic acid, perbenzoic acid, peracetic acid, and m-chloroperoxybenzoic acid. Suitable solvents include halogenated hydrocarbons, e.g., dichloromethane. Alternatively, the compounds of Formula I wherein p is 1 may be prepared using N-oxide derivatives of the starting materials or intermediates.

Compounds of Formula I wherein p is 0 (compounds of Formula I wherein the cyclic amine portion of $R^2$ is not in the N-oxide form) may also be prepared by reduction of the corresponding compound of Formula I wherein p is 1. The reduction is carried out under standard conditions with an appropriate reducing agent in a suitable solvent. The mixture is occasionally agitated while the reaction temperature is gradually increased over a range of 0° C. to 80° C. Appropriate reducing agents include sulfur, sulfur dioxide, triaryl phosphines (e.g., triphenyl phosphine), alkali boranates (e.g., lithium, sodium boranate, etc.), phosphorous trichloride and tribromide. Suitable solvents include acetonitrile, ethanol or aqueous diozane.

As will be apparent to one of ordinary skill in the art, compounds of Formula I may be prepared as individual optical isomers or as mixtures, racemic or otherwise, thereof, depending on the reactants employed in their preparation. For example, the individual enantiomers of a compound of Formula I may be prepared by reacting the racemic mixture with an optically active resolving agent to form a pair of diastereomeric compounds. Diastereomers have distinct physical properties (e.g., melting points, boiling points, solubilities, reactivity, etc.) and can be readily separated by taking advantage of these dissimilarities. For example, the diastereomers may be separated by chromatography or, preferably, by separation/resolution techniques based upon differences in solubility. The optically pure enantiomer is than recovered, along with the resolving agent, by any practical means that would not result in racemization.

While resolution of enantiomers may be carried out using covalent diastereomeric derivatives of compounds of Formula I, dissociable complexes are preferred, e.g., crystalline diastereomeric salts. In that compounds of Formula I contain basic amine groups, such crystalline diastereomeric salts may be prepared by using an optically active acid as the resolving agent. Suitable resolving acids include tartaric acid, o-nitrotartranilic acid, mandelic acid, malic acid, the 2-arylpropionic acids in general, and camphorsulfonic acid.

Individual enantiomers of compounds of Formula I may also be separated by such methods as direct or selective crystallization or by any other method known to one of ordinary skill in the art. A more detailed description of the techniques applicable to the resolution of stereoisomers of compounds of Formula I can be found in Jean Jacques, Andre Collet, Samuel H. Wilen, Enantiomers, Racemates and Resolutions, John Wiley & Sons, Inc. (1981). Alternatively, individual isomers of compounds of Formula I may be prepared using optically active starting materials.

As will be apparent to one of ordinary skill in the art, compounds of Formula I may be prepared as individual diastereomers. For example, a compound of Formula I that may exist as the endo or exo form, e.g., when the $R^2$ is 1-azabicyclo[3.3.1]non-4-yl, and in which the $R^2$ substituent exhibits a chiral center at the ring carbon which is bonded to the α-oxoacetmide nitrogen, two separate enantiomeric pairs are possible, i.e., the (RS)-endo- and (RS)-exp-racemates. The enantiomers of each pair, relative to those of the other pairs, are diastereomers, i.e., nonsuperimposable stereoisomers.

Once the diastereomers are separated into enantiomeric pairs, the pure enantiomers may be resolved by any of the techniques described above. Alternatively, individual isomers of compounds of Formula I may be prepared using stereoisomeric forms of the starting materials.

Compounds of Formula I may be converted to the corresponding acid addition salt with a pharmaceutically acceptable inorganic or organic acid. In addition, compounds of Formula I wherein X and/or Y hydroxy substituents form salts may be prepared with a pharmaceutically acceptable inorganic or organic base. Inorganic and organic acids and bases suitable for the preparation of the pharmaceutically acceptable salts of compounds of Formula I are set forth in the definitions section of this application.

Compounds of Formula I in the acid addition salt form may be converted to the corresponding free base by treatment with a suitable base such as ammonium hydroxide solution, sodium hydroxide or the like. Compounds of Formula I wherein X and/or Y hydroxy substituents form salts may be converted to the corresponding free base by treatment with a suitable acid such as hydrochloric acid.

Of the processes for synthesizing compounds of Formula I described within this application, certain methods are preferred. Presently, the preferred mode of synthesis is the procedure in which an α-oxoacetic acid derivative of Formula II, wherein $R^8$ is halogen, is reacted with an amine of the formula $NHR^2R^3$ A less preferred method is carried out by proceeding as above but replacing the α-oxoacetyl halogen with an α-oxoacetic acid or ester. While compounds of Formula I may also be synthesized by the alkylation processes described in Scheme III, these procedures may require more severe reaction conditions and are usually restricted to alkylation of unsubstituted amides with primary alkylating agents, e.g., $CH_3L$.

In summary, the processes for preparing the compounds of Formula I are (1) reacting an optionally substituted α-oxoacetic acid derivative, preferably an α-oxoacetyl halogen, of Formula II with an appropriate substituted amine of the formula $NHR^2R^3$ to form a compound of Formula I;

(2) reacting an α-chloro-α-oxoacetamide of Formula III with optionally substituted benzene, indole, benzimidazolidinone, benzothiophene or benzofuran to form a compound of Formula I;

(3) reacting an optionally substituted α-oxoacetic acid derivative, preferably an α-oxoacetyl chloride, of Formula II with an appropriate substituted amine of the formula $NH_2R^3$, wherein $R^3$ is hydrogen or lower alkyl, to form an α-oxoacetamide of Formula IV;

(4) optionally alkylating a compound of Formula IV, wherein $R^3$ is hydrogen, with an alkylating agent of the formula $R^3L$, wherein $R^3$ is lower alkyl, to form a compound of Formula IV wherein $R^3$ is lower alkyl;

(5) reacting an optionally substituted compound of Formula IV with an alkylating agent of the formula $R^2L$ to form a compound of Formula I;

(6) optionally alkylating a compound of Formula I, wherein $R^3$ is hydrogen, with an alkylating agent of the formula $R^3L$, wherein $R^3$ is lower alkyl, to form a compound of Formula I wherein $R^3$ is lower alkyl;

(7) optionally hydrogenating a compound of Formula I in which R is Formula (b) wherein the optional bond is present to form the corresponding compound wherein the optional bond is absent;

(8) optionally reacting with or exchanging substituents present on a compound of Formula I to form an additional substituted compound of Formula I;

(9) optionally converting the acid salt of a compound of Formula I to the corresponding pharmaceutically acceptable free base;

(10) optionally converting the free base of a compound of Formula I to the corresponding pharmaceutically acceptable salt;

(11) optionally oxidizing a compound of Formula I wherein p is 0 to the corresponding N-oxide wherein p is 1;

(12) optionally reducing the N-oxide of a compound of Formula I wherein p is 1 to the corresponding compound of Formula I wherein p is 0; or

(13) optionally separating a mixture of isomers of a compound of Formula I into a single isomer.

In any of the above processes, a reference to Formula I, II, III and IV refers to such Formula wherein X, Y, Z, $R^1$, $R^2$, $R^3$, $R^4$, $R^5$, $R^6$, $R^7$, $R^8$, n, p, q and t have the broadest definitions set forth in the Summary of the Invention, with the processes applying particularly well to the presently preferred embodiments.

EXAMPLE 1

1-Methyl-α-oxo-3-indoleacetyl chloride

The following is the preparation of a compound of Formula II in which

R$^1$ is Formula (d);
X and Y are hydrogen;
Z is —N(CH$_3$)—; and
R$^5$ is hydrogen.

1-Methylindole (6.8 g; 52.5 mmol) was dissolved in 100 ml of ether. The solution was stirred under a nitrogen atmosphere while α-oxo-α-chloroacetyl chloride (7.6 g; 60.3 mmol) was added in approximately 0.5 ml aliquots via a syringe. The reaction mixture was stirred for an additional 30 minutes at ambient temperature and then cooled in an ice bath. The product was collected as a precipitate on a sintered funnel and dried to yield 10.8 g (48.7 mmol) of 1-methyl α-oxo-3-indoleacetyl chloride, m.p. 122°-133° C.

Proceeding as in Example 1 but replacing 1-methylindole with indole, α-oxo-3-indoleacetyl chloride, m.p. 133°-134° C., was prepared.

EXAMPLE 2

(S)-N-(Azabicyclo[2.2.2]oct-3-yl)-1-methyl-α-oxo-3-indoleacetamide

The following is the preparation of a compound of Formula I in which

R$^1$ is Formula (d);
R$^3$ is hydrogen;
X and Y are hydrogen;
Z is —N(CH$_3$)—; and
R$^2$ is (S)-1-azabicyclo[2.2.2]oct-3-yl.

(S)-3-amino-1-azabicyclo[2.2.2]octane dihydrochloride salt (7.5 g; 37.5 mmol) and sodium hydroxide (2.0 g; 50.0 mmols) were dissolved in 50 ml of water. The solution was cooled in an ice bath and 100 ml of methylene chloride was added. The mixture was stirred while approximately one third of a solution containing 1-methy-α-oxo-3-indoleacetyl chloride (10.8 g; 48.7 mmol) was added in a dropwise fashion, after which additional sodium hydroxide (3.0 g; 75.0 mmol) in 20.0 ml of water was mixed in. The remaining 1-methy-α-oxo-3-indoleacetyl chloride was then added and the reaction mixture was stirred for 10 minutes. The aqueous layer was then separated from the organic phase and rinsed with methylene chloride. The combined organic phase was dried over potassium carbonate. Filtration and evaporation of the solvent resulted in 5.1 g of crude product. The crude product was purified by chromatography (silica gel 60; 7% MeOH in CH$_2$Cl$_2$ containing approximately 0.5% NH$_4$OH) to yield 3.6 g (11.5 mmol) of (S)-N-(1-azabicyclo[2.2.2]oct-3-yl)-1-methyl-α-oxo-3-indoleacetamide, m.p. 186°-187° C., $[\alpha]_D^{25}$ −41° (CHCl$_3$).

Hydrogen chloride (approximately 850 mg) in 8.5 ml of ethanol was added to 80 ml of hot ethanol containing (S)-N-(1-azabicyclo[2 2.2]oct-3-yl)-1-methyl-α-oxo-3-indoleacetamide (3.6 g; 11.5 mmmol), to yield 3.2 g (9.2 mmol) of (S)-N-(1-azabicyclo[2.2.2]oct-3-yl)-1-methyl-α-oxo-3-indoleacetamide hydrochloride, m.p. 307°-308° C., $[\alpha]_D^{25}$ −16° (H$_2$O).

Proceeding as in Example 2 but replacing (S)-3-amino-1-azabicyclo[2.2.2]octane with (R)-3-amino-1-azabicyclo[2.2.2]octane, (R)-N-(1-azabicyclo[2.2.2]oct-3-yl)-1-methyl-α-oxo-3-indoleacetamide, m.p. 187°-189° C., $[\alpha]_D^{25}$ −41° (CHCl$_3$), and (R)-3-(1-azabicyclo[2.2.2]oct-3-yl)-1-methyl-α-oxo-3-indoleacetamide hydrochloride, m.p. 307°-308° C., $[\alpha]_D^{25}$ +18° (H$_2$O), were prepared.

Proceeding as in Example 2 but replacing 1-methyl-α-oxo-3-indoleacetyl chloride with 5-chloro-α-oxo-3-indoleacetyl chloride, (S)-N-(1-azabicyclo[2.2.2]oct-3-yl)-5-chloro-α-oxo-3-indoleacetamide hydrochloride, m.p. 309°-310° C., $[\alpha]_D^{25}$ −8.6° (H$_2$O), was prepared.

Proceeding as in Example 2 but replacing (S)-3-amino-1-azabicyclo[2.2.2]octane with (R)-3-amino-1-azabicyclo[2.2.2]octane and 1-methy-α-oxo-3-indoleacetyl chloride with 5-chloro-α-oxo-3-indoleacetyl chloride, (R)-N-(1-azabicyclo[2.2.2]oct-3-yl)-5-chloro-α-oxo-3-indoleacetamide hydrochloride, m.p. 310° C., $[\alpha]_D^{25}$ +8.0° (H$_2$O), was prepared.

Proceeding as in Example 2 but replacing 1-methyl-α-oxo-3-indoleacetyl chloride with 1-methyl-5-bromo-α-3-indoleacetyl chloride, (S)-N-(1-azabicyclo[2.2.2]oct-3-yl)-1-methyl-5-bromo-α-oxo-3-indoleacetamide hydrochloride, m.p. 239°-242° C., $[\alpha]_D^{25}$ −5.4° (H$_2$O), was prepared.

Proceeding as in Example 2 but replacing (S)-3-amino-1-azabicyclo[2.2.2]octane with (RS)-3-amino-1-azabicyclo[2.2.2]octane and 1-methyl-α-oxo-3-indoleacetyl chloride with 1-methyl-5-benzyloxy-α-oxo-3-indoleacetyl chloride, (RS)-N-(1-azabicyclo[2.2.2]oct-3-yl)-1-methyl-5-benzyloxy-α-oxo-3-indoleacetamide was prepared.

Proceeding as in Example 2 but replacing 1-methyl-α-oxo-3-indoleacetyl chloride with 1-methyl-4-methoxy-α-oxo-3-indoleacetyl chloride, (S)-N-(1-azabicyclo[2.2.2]oct-3-yl)-1-methyl-4-methoxy-α-oxo-3-indoleacetamide hydrochloride, m.p. 263°-265° C., $[\alpha]_D^{25}$ −19.9° (H$_2$O), was prepared.

Proceeding as in Example 2 but replacing 1-methyl-α-oxo-3-indoleacetyl chloride with 1-methyl-5-methoxy-α-oxo-3-indoleacetyl chloride, (S)-N-(1-azabicyclo[2.2.2]oct-3-yl)-1-methyl-5-methoxy-α-oxo-3-indoleacetamide hydrochloride, m.p. 246°-249° C., $[\alpha]_D^{25}$ −34.9° (H$_2$O), was prepared.

Proceeding as in Example 3 but replacing (S)-3-amino-1-azabicyclo[2.2.2]octane with (RS)-3-amino-1-azabicyclo[2.2.2]octane and 1-methyl-α-oxo-3-indoleacetyl chloride with 1-methyl-5-methoxy-α-oxo-3-indoleacetyl chloride, (RS)-N-(1-azabicyclo[2.2.2]oct-3-yl)-1-methyl-5-methoxy-α-oxo-3-indoleacetamide maleate, m.p. 96°-97° C., was prepared.

Proceeding as in Example 2 but replacing 1-methyl-α-oxo-3-indoleacetyl chloride with 1,7-dimethyl-α-oxo-3-indoleacetyl chloride, (S)-N-(1-azabicyclo[2.2.2]oct-3-yl)-1,7-dimethyl-α-oxo-3-indoleacetamide hydrochloride, m.p. 275°-276° C., $[\alpha]_D^{25}$ −13.3° (H$_2$O), was prepared.

Proceeding as in Example 2 but replacing 1-methyl-α-oxo-3-indoleacetyl chloride with 1,2-dimethyl-α-oxo-3-indoleacetyl chloride, (S)-N-(1-azabicyclo[2.2.2]oct-3-yl)-1,2-dimethyl-α-oxo-3-indoleacetamide hydrochloride, m.p. 292°-295° C., $[\alpha]_D^{25}$ −21.9° (H$_2$O), was prepared.

Proceeding as in Example 2 the following may be prepared:

N-(1-azabicyclo[2.2.2]oct-3-yl)-α-oxo-benzeneacetamide;

N-(1-azabicyclo[2.2.2]oct-4-yl)-α-oxo-benzeneacetamide;

endo-N-(9-methyl-9-azabicyclo[3.3.1]non-3-yl)-α-oxo-benzeneacetamide;

exo-N-(9-methyl-9-azabicyclo[3.3.1]non-3-yl)-α-oxo-benzeneacetamide;
endo-N-(8-methyl-8-azabicyclo[3.2.1]oct-3-yl)-α-oxo-benzeneacetamide
exo-N-(8-methyl-8-azabicyclo[3.2.1]oct-3-yl)-α-oxo-benzeneacetamide;
endo-N-(1-azabicyclo[3.3.1]non-4-yl) α-oxo-benzeneacetamide;
exo-N-(1-azabicyclo[3.3.1]non-4-yl) α-oxo-benzeneacetamide;
N-(1-azabicyclo[2.2.2]oct-3-yl) α-oxo-1-indoleacetamide;
N-(1-azabicyclo[2.2.2]oct-4-yl) α-oxo-1-indoleacetamide;
endo-N-(9-methyl-9-azabicyclo[3.3.1]non-3-yl) α-oxo-1-indoleacetamide;
exo-N-(9-methyl-9-azabicyclo[3.3.1]non-3-yl)-α-oxo-1-indoleacetamide;
endo-N-(8-methyl-8-azabicyclo[3.2.1]oct-3-yl) α-oxo-1-indoleacetamide;
exo-N-(8-methyl-8-azabicyclo[3.2.1]oct-3-yl) α-oxo-1-indoleacetamide;
endo-N-(1-azabicyclo[3.3.1]non-4-yl) α-oxo-1-indoleacetamide;
exo-N-(1-azabicyclo[3.3.1]non-4-yl) α-oxo-1-indoleacetamide;
(1-azabicyclo[2.2.2]oct-3-yl)-α-oxo-1-benzimidazolidinoneacetamide;
N-(1-azabicyclo[2.2.2]oct-4-yl)-α-oxo-3-benzimidazolidinoneacetamide;
endo-N-(9-methyl-9-azabicyclo[3.3.1]non-3-yl)-oxo-1-benzimidazolidinoneacetamide;
exo-N-(9-methyl-9-azabicyclo[3.3.1]non-3-yl)-oxo-1-benzimidazolidinoneacetamide;
endo-N-(8-methyl-8-azabicyclo[3.2.1]oct-3-yl)-oxo-1-benzimidazolidinoneacetamide;
exo-N-(8-methyl-8-azabicyclo[3.2.1]oct-3-yl)-oxo-1-benzimidazolidinoneacetamide;
endo-N-(1-azabicyclo[3.3.1]non-4-yl)-oxo-1-benzimidazolidinoneacetamide;
exo-N-(1-azabicyclo[3.3.1]non-4-yl)-oxo-1-benzimidazolidinoneacetamide;
N-(1-azabicyclo[2.2.2]oct-3-yl)-α-oxo-3-benzothiopheneacetamide;
N-(1-azabicyclo[2.2.2]oct-4-yl)-α-oxo-3-benzothiopheneacetamide;
endo-N-(9-methyl-9-azabicyclo[3.3.1]non-3-yl)-α-oxo-3-benzothiopheneacetamide;
exo-N-(9-methyl-9-azabicyclo[3.3.1]non-3-yl)-α-oxo-3-benzothiopheneacetamide;
endo-N-(8-methyl-8-azabicyclo[3.2.1]oct-3-yl)-α-oxo-3-benzothiopheneacetamide:
exo-N-(8-methyl-8-azabicyclo[3.2.1]oct-3-yl)-α-oxo-3-benzothiopheneacetamide;
endo-N-(1-azabicyclo[3.3.1]non-4-yl)-α-oxo-3-benzothiopheneacetamide;
exo-N-(1-azabicyclo[3.3.1]non-4-yl)-α-oxo-3-benzothiopheneacetamide;
N-(1-azabicyclo[2.2.2]oct-3-yl)-α-oxo-3-benzofuranacetamide;
N-(1-azabicyclo[2.2.2]oct-4-yl)-α-oxo-3-benzofuranacetamide;
endo-N-(9-methyl-9-azabicyclo[3.3.1]non-3-yl)-α-oxo-3-benzofuranacetamide;
exo-N-(9-methyl-9-azabicyclo[3.3.1]non-3-yl)-α-oxo-3-benzofuranacetamide;
endo-N-(8-methyl-8-azabicyclo[3.2.1]oct-3-yl)-α-oxo-3-benzofuranacetamide;
exo-N-(8-methyl-8-azabicyclo[3.2.1]oct-3-yl)-α-oxo-3-benzofuranacetamide;
endo-N-(1-azabicyclo[3.3.1]non-4-yl)-α-oxo-3-benzofuranacetamide;
exo-N-(1-azabicyclo[3.3.1]non-4-yl)-α-oxo-3-benzofuranacetamide;
endo-N-(9-methyl-9-azabicyclo[3.3.1]non-3-yl)-α-oxo-3-indoleacetamide;
exo-N-(9-methyl-9-azabicyclo[3.3.1]non-3-yl)-α-oxo-3-indoleacetamide;
exo-N-(8-methyl-8-azabicyclo[3.2.1]oct-3-yl)-α-oxo-3-indoleacetamide;
exo-N-(1-azabicyclo[3.3.1]non-4-yl)-α-oxo-3-indoleacetamide;
N-(1-azabicyclo[2.2.2]oct-3-yl)-1,2,3,4,-tetrahydro-α-oxo-10-pyrido[1,2-a]indoleacetamide;
N-(1-azabicyclo[2.2.2]oct-4-yl)-1,2,3,4,-tetrahydro-α-oxo-10-pyrido[1,2-a]indoleacetamide;
endo-N-(9-methyl-9-azabicyclo[3.3.1]non-3-yl)-1,2,3,4,-tetrahydro-α-oxo-10-pyrido[1,2-a]indoleacetamide;
exo-N-(9-methyl-9-azabicyclo[3.3.1]non-3-yl)-1,2,3,4,-tetrahydro-α-oxo-10-pyrido[1,2-a]indoleacetamide;
endo-N-(8-methyl-8-azabicyclo[3.2.1]oct-3-yl)-1,2,3,4,-tetrahydro-α-oxo-10-pyrido[1,2-a]indoleacetamide;
exo-N-(8-methyl-8-azabicyclo[3.2.1]oct-3-yl)-1,2,3,4,-tetrahydro-α-oxo-10-pyrido[1,2-a]indoleacetamide;
endo-N-(1-azabicyclo[3.3.1]non-4-yl)-1,2,3,4,-tetrahydro-α-oxo-10-pyrido[1,2-a]indoleacetamide; and
exo-N-(1-azabicyclo[3.3.1]non-4-yl)-1,2,3,4,-tetrahydro-α-oxo-10-pyrido[1,2-a]indoleacetamide.

EXAMPLE 3 endo-N-(8-methyl-8-azabicyclo[3.2.1]oct-3-yl)-1-methyl-α-oxo-3-indoleacetamide

The following is the Preparation of a compound of Formula I in which
X and Y are hydrogen;
$R^1$ is Formula (d);
Z is —N(CH$_3$)—; and
$R^3$ is endo-8-methyl-8-azabicyclo[3.2.1]oct-3-yl.

1-methyl-α-oxo-3-indoleacetyl chloride (1.0 g; 4.8 mmol) in 40 ml of methylene chloride was mixed with 40 ml of methylene chloride containing endo-3-amino-8-methyl-8-azabicyclo[3.2.1]octane (675 mg; 4.8 mmoles). The reaction mixture was stirred at ambient temperature for 16 hours and at reflux temperature for an additional 4 hours. The mixture was allowed to cool to ambient temperature and then mixed with a solution of saturated sodium bicarbonate and stirred form 30 minutes. The organic phase was separated, dried over potassium carbonate, filtered and concentrated. The resulting product was dissolved in 5 to 10 ml of hot ethanol and acidified with hydrogen chloride (200 mg) in 2 ml of ethanol. The solution was cooled and the product crystallized to yield 1.38 g (3.8 mmol) of endo-N-(8-methyl-8-azabicyclo[3.2.1]oct-3-yl)-1-methyl-α-oxo-3-indoleacetamide hydrochloride, m.p. 308°–310° C.

Proceeding as in Example 3 but replacing endo-3-amino-8-methyl-8-azabicyclo[3.2.1]octane with
(RS)-3-amino-1-azabicyclo[2.2.2]octane,
(RS)-N-(1-azabicyclo[2.2.2]oct-3-yl)-1-methyl-α-oxo-3-indoleacetamide, m.p. 235°–237° C.,
(RS)-N-(1-azabicyclo[2.2.2]oct-3-yl)-1-methyl-α-oxo-3-indoleacetamide hydrochloride, m.p. 295°–298° C., and (RS)-N-(1-azabicyclo[2.2.2]oct-3-yl)-1-methyl-α-oxo-3-indoleacetamide maleate, m.p. 175°-178° C., were prepared. were prepared.

Proceeding as in Example 3 but replacing endo-3-amino-8-methyl-8-azabicyclo[3.2.1]octane with (RS)-3-amino-1-azabicyclo[2.2.2]octane and 1-methyl α-oxo-3-indoleacetyl chloride with α-oxo-3-indoleacetyl chloride, (RS)-N-(1-azabicyclo[2.2.2]oct-3-yl)-α-oxo-3-indoleacetamide hydrochloride, m.p. 175°-177° C., was prepared.

Proceeding as in Example 3 but replacing endo-3-amino-8-methyl-8-azabicyclo[3.2.1]octane with (RS)-3-methylamino-1-azabicyclo[2.2.2]octane, (RS)-N-(1-azabicyclo[2 2.2]oct-3-yl)-N-methyl-1-methyl-α-oxo-3-indoleacetamide hydrochloride, m.p. 192°-195° C., was prepared.

Proceeding as in Example 3 but replacing endo-3-amino-8-methyl-8-azabicyclo[3.2.1]octane with 4-amino-1-azabicyclo[2.2.2]octane, N-(1-azabicyclo[2.2.2]oct-4-yl)-α-oxo-3-indoleacetamide hydrochloride, m.p. 319°-320° C., was prepared.

Proceeding as in Example 3 but replacing endo-3-amino-8-methyl-8-azabicyclo[3.2.1]octane with (RS)-endo-4-amino-1-azabicyclo[3.3.1]nonane and 1-methyl-α-oxo-3-indoleacetyl chloride with 1-methyl-5-methoxy-α-oxo-3-indoleacetyl chloride, (RS)-endo-N-(1-azabicyclo[3.3.1]non-4-yl)-5-methoxy-α-oxo-3-indoleacetamide hydrochloride, m.p 298°-300° C., was prepared.

Proceeding as in Example 3 but replacing endo-3-amino-8-methyl-8-azabicyclo[3.2.1]octane with (RS)-3-amino-1-azabicyclo[2.2.2]octane and 1-methyl-α-oxo-3-indoleacetyl chloride with 1-methyl-5-cyano-α-oxo-3-indoleacetyl chloride, (RS)-N-(1-azabicyclo[3.3.1]non-3-yl)-5-cyano-α-oxo-3-indoleacetamide hydrochloride, m.p. 232°-235° C., was prepared.

EXAMPLE 4

(RS)-N-(1-azabicyclo[2.2.2]oct-3-yl)-5-hydroxy-α-oxo-3-indoleacetamide

The following is the preparation of a compound of Formula I in which
X is hydroxy in the 5-position;
Y is hydrogen;
$R^1$ is Formula (d);
Z is —NH—; and
$R^3$ is (RS)-1-azabicyclo[2.2.2]oct-3-yl.

(RS)-N-(1-azabicyclo[2.2.2]oct-3-yl)-5-benzyloxy-α-oxo-3-indoleacetamide (500 mg; 1.27 mmol) in 50 ml of methanol was hydrogenated over 10% palladium on carbon (100 mg) for 16 hours under hydrogen atmosphere at 50 psi. The catalyst was removed by filtration and the filtrate was acidified with 10% hydrogen chloride in ethanol. The solution is concentrated and the product recrystallized from ethanol to yield 163 mg (0.45 mmol) of (RS)-N-(1-azabicyclo[2.2.2]oct-3-yl)-5-hydroxy-α-oxo-3-indoleacetamide hydrochloride, m.p. 291°-292° C.

EXAMPLE 5

(S)-N-(1-azabicyclo[2.2.2]oct-3-yl)-1-methyl-5-hydroxy-α-oxo-3-indoleacetamide

The following is the preparation of a compound of Formula I in which
X is hydroxy in the 5-position;
Y is hydrogen;
$R^1$ is Formula (d);
Z is —N(CH$_3$)—; and
$R^3$ is (S)-1-azabicyclo[2.2.2]oct-3-yl.

(S)-N-(1-azabicyclo[2.2.2]oct-3-yl)-1-methyl-5-methoxy-α-oxo-3-indoleacetamide chloride (750 ml; 2.2 mmol) in 30 ml of methylene chloride was stirred and cooled to −70° C. A 1M solution of boron tribromide in methlene chloride (8.0 ml; 8.0 mmol) was added via a syringe. The solution was allowed to warm to ambient temperature and then stirred continuely for 4 days. The reaction mixture was then stirred for 1 hour with ice-cold water containing an excess of potassium carbonate. The layers were separated and the phenolic product was extracted from the methylene chloride layer into 5% aqueous sodium hydroxide. The aqueous layer was stirred and sodium bicarbonate was added until saturated. The product that precipitated was extracted into methylene chloride. The methylene chloride solution was dried over potassium carbonate, filtered and concentrated to leave 500 ml (1.5 mmol) of (S)-N-(1-azabicyclo[2.2.2]oct-3-yl)-1-methyl-5-hydroxy-α-oxo-3-indoleacetamide chloride, m.p. 282°-284° C., $[\alpha]_D^{25}$ −7.8° (H$_2$O).

EXAMPLE 6

Oral Formulation

A representative solution for oral administration contains:

| | |
|---|---|
| A compound of Formula I | 100-1000 mg |
| Citric Acid Mono hydrate | 105 mg |
| Sodium Hydroxide | 18 mg |
| Flavouring | q.s. |
| Water | to 100 ml |

Intravenous Formulation

A representative solution for intravenous administration contains:

| | |
|---|---|
| A compound of Formula I | 10-100 mg |
| Dextrose Monohydrate | q.s to make isotonic |
| Citric Acid Monohydrate | 1.05 mg |
| Sodium Hydroxide | 0.18 mg |
| Water for Injection | to 1.0 ml |

EXAMPLE 7

5-HT$_3$ Receptor Screening Assay

The following describes an in vitro assay for determining the 5-HT$_3$ receptor binding affinity of compounds of Formula I. The method is essentially that described by Kilpatrick et al., previously cited, which measures the affinity for 5-HT$_3$ receptors of the rat cerebral cortex radiolabelled with [$^3$H]quipazine.

Membranes are prepared from the cerebral cortices of rat brains homogenized in 50 mM Tris buffer (pH 7.4 at 4° C.) using a Polytron P10 tissue disrupter (setting 10, 2×10 sec bursts). The homogenate is centrifuged at 48,000×g for 12 min and the pellet obtained is washed, by resuspension and centrifugation, three times in homogenizing buffer. The tissue pellets are resuspended in the assay buffer, and are stored under liquid nitrogen until required.

The binding assays are conducted using a Tris-Krebs assay buffer of the following composition (mM): NaCl, 154; KCl, 5.4; KH$_2$PO$_4$, 1.2; CaCl$_2$.2H$_2$O, 2.5; MgCl$_2$, 1.0; glucose, 11; Tris, 10. Assays are conducted at 25° C. at 7.4 in a final volume of 0.25 ml. Zacopride (1.0 μM) is used to define the non-specific binding (NSB). 5-HT$_3$ receptors present in rat cortical membranes are labelled using 0.3–0.7 nM [$^3$H]quipazine (specific activity 50–66 Ci/mmol; New England Nuclear) in the presence of 0.1 μM paroxetine to prevent [$^3$H]quipazine binding to 5-HT uptake sites. The rat cortex membranes are incubated with [$^3$H]quipazine in the presence of 10 different concentrations of test compound ranging from $1\times10^{-12}$ to $1\times10^{-4}$ molar. Incubations are conducted for 45 min at 25° C. and are terminated by vacuum filtration over Whatman GF/B glass fiber filters using a Brandel 48 well cell harvester. After filtration the filters are washed for 8 sec with 0.1M NaCl. The filters are pretreated with 0.3% polyethyleneimine 18 hr prior to use in order to reduce filter binding of the radioligand. Radioactivity retained on the filters is determined by liquid scintillation counting.

The concentration of test compound producing 50% inhibition of radioligand binding is determined by an iterative curve fitting procedure. Affinities are expressed as the negative logarithm of the IC$_{50}$ value (pIC$_{50}$). Compounds of Formula I exhibit 5-HT$_3$ receptor binding affinity, i.e., pIC$_{50}$ values greater than 6.

EXAMPLE 8

5-HT$_3$ Antagonist Activity in Rats (Von Bezold-Jarisch Reflex)

The following describes an in vivo method for determining the 5-HT$_3$ antagonist activity of compounds of Formula I. The method is a modified version of that described by Butler et al., Cohen et al., and Fozard, all previously cited, in which the 5-HT$_3$ selective agonist 2-methyl-5-hydroxytryptamine (2-m-5-HT) is substituted for 5-HT.

Male Sprague-Dawley rats, 250–380 grams, are anesthetized with urethane (1.4 g/kg, i.p.). A tracheotomy is performed and a tube is inserted into the trachea to facilitate respiration. Jugular and femoral veins are canulated for intravenous administration of drug. The duodenum is canulated for intraduodenal administration of drug. Heart rate is monitored by Gould ECG/Biotech amplifiers. After at least a 30 min equilibration period and prior to administration of test compound, control responses to intravenous administration of 2-m-5-HT are determined and a minimal dose producing sufficient and consistent bradycardia is chosen.

Potency

Intravenous challenges to 2-m-5-HT are administered every 12 minutes. Either vehicle or test compound is administered intravenously 5 minutes before each challenge to 2-m-5-HT. Each successive administration of test compound is increased in dosage until responses to 2-m-5-HT are blocked.

Duration

Vehicle or test compound is administered intravenously or intraduodenally and subsequent challenges to 2-m-5-HT are administered at 5, 15, 30, 60, 120, 180, 240, 300 and, in some instances, 360, 420 and 480 minutes post dose.

For both potency and duration studies heart rate (beats/min) is recorded continuously for the duration of the study Responses to 2-m-5-HT are represented by the peak decrease in heart rate Effects of test compounds are represented as percent inhibition of the bradycardia induced by 2-m-5-HT. Data are analyzed by a one-way repeated measures ANOVA and followed by pairwise comparison to vehicle control using Fisher's LSD strategy From a dose-response curve so constructed, an ID$_{50}$ value is obtained to represent the dose that inhibited 50% of the bradycardia induced by 2-m-5HT Compounds of Formula I exhibit 5-HT$_3$ receptor antagonist activity in this assay, i.e., ID$_{50}$ values less than 3.0 mg/kg, i.v.

EXAMPLE 9

Cisplatin-induced Emesis in Ferrets

The following describes the procedure for determining the intravenous (i.v.) effects of compounds of Formula I on cisplatin-induced emesis in ferrets.

Adult, male, castrated ferrets are allowed food and water ad libitum both prior to and throughout the testing period. Each animal is randomly chosen and anesthetized with a metofane/oxygen mixture, weighed and assigned to one of three test groups. While anesthetized an incision is made along the ventral cervical region approximately two to four centimeters in length. The jugular vein is then isolated and cannulated with a capped saline filled PE-50 polyethylene tubing. The cannula is exteriorized at the base of the skull and the incision closed with wound clips. The animals are then returned to their cages and allowed to recover from anesthesia prior to commencement of the study.

Vehicle or test compound is administered i.v. at 1.0 ml/kg and 1.0 mg/kg, respectively. Within 2.0 minutes of the administration of vehicle or test compound, cisplatin is injected i.v. at 10 mg/kg. The animals are then observed continuously for a 5 hour period and emetic responses (i.e., vomiting and/or retching) are recorded. For purposes of this example and that of Example 11, vomiting is defined as the successful evacuation of stomach contents and a single episode of retching is defined as rapid and successive efforts to vomit occurring within a one minute time period.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

Intravenously administered compounds of Formula I are anti-emetic in this assay.

Proceeding as in Example 10 but administering the test compounds by oral route, the anti-emetic effects of compounds of Formula I may be evaluated. Orally administered compounds of Formula I are anti-emetic in this assay.

EXAMPLE 10

Cisplatin-induced Emesis in Dogs

The following describes the procedure for determining the intravenous (i.v.) effects of compounds of Formula I on cisplatin-induced emesis in dogs.

Male and female dogs (6–15 kg) are fed one cup of dry dog food. One hour following feeding, cisplatin (cis-diamminedichloroplatinum) is administered i.v. at 3 mg/kg. Sixty minutes after the administration of cisplatin, either vehicle or test compound is injected i.v. at 0.1 ml/kg and 1.0 mg/kg, respectively. The dogs are then observed continuously for a 5 hour period and the emetic responses (i.e., vomiting and/or retching) are recorded.

Emetic responses are represented as (1) time to onset of emesis, (2) total vomiting episodes,and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

Compounds of Formula I exhibit anti-emetic activity in this assay.

EXAMPLE 11

Gastric Emptying of Test Meal in Rats

The following describes an in vivo method of determining the prokinetic activity of the compounds of Formula I by measuring the rate of gastric emptying of test meal in rats. The method is that described by Droppleman et al., previously cited.

Test meal is prepared by slowly adding 20 grams of cellulose gum (Hercules Inc., Wilmington, Delaware) to 200 ml of cold distilled water that is being mixed in a Waring blender at approximately 20,000 rpm. Mixing continues until complete dispersion and hydration of the cellulose gum takes place (approximately 5 min). Three beef bouillon cubes are dissolved in 100 ml of warm water and then blended into the cellulose solution followed by 16 g of purified casein (Sigma Chemical Co., St. Louis, Mo.), 8 g of Powdered confectioners sugar, 8 g of cornstarch, and 1 g of powdered charcoal. Each ingredient is added slowly and mixed thoroughly resulting in approximately 325 ml of a dark gray to black, homogenous paste. The meal is then refrigerated overnight during which time trapped air escapes. Prior to the assay the meal is removed from the refrigerator and allowed to warm to room temperature.

Mature (170 to 204 g) male Sprague-Dawley rats are deprived of food for 24 hours with water ad libitum. On the morning of the study each animal is weighed and randomly assigned to treatment groups consisting of ten animals per group. Each rat receives either vehicle, test compound or the reference standard metoclopramide by intraperitoneal injection. At 0.5 hours post injection 3.0 ml of test meal is orally administered to each rat with a 5.0 ml disposable syringe. Five test meal samples are weighed on an analytical balance and these weights are averaged to find a mean test meal weight. At 1.5 hours post injection each rat is sacrificed by carbon dioxide asphyxiation and the stomach is removed by opening the abdomen and carefully clamping and cutting the esophagus just below the pyloric sphincter. Taking care not to lose any of the its contents, each stomach is placed on a small, pre-weighed and correspondingly labeled 7 ml weigh boat and immediately weighed on an analytical balance. Each stomach is then cut open along the lesser curvature, rinsed with tap water, gently blotted dry to remove excess moisture and weighed. The amount of test meal remaining in the stomach is represented by the difference between the weight of the full stomach and the weight of the stomach empty. The difference between the amount of test meal remaining and the mean test meal weight represents the quantity of test meal that empties during the 1.5 hour post injection period.

Responses are represented as grams of meal emptied or percent change from control. Means and standard deviations of the test groups are compared to those of the reference groups. Significance is determined via Dunnett's t-test (Statistical Association Journal, December 1955, 1096–112).

Compounds of Formula I exhibit prokinetic activity in this assay.

EXAMPLE 12

The Mouse Anxiolytic Behavior Model

The following describes an in vivo method for determining anxiolytic activity of compounds of Formula I.

Naive male C5BI/6J mice, 18–20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin (1980), as described in Kilfoil et al., cited previously. Briefly, the chamber consists of a plexiglass box (44×21×21 cm), divided into two chambers by a black plexiglass partition. The partition dividing the two chambers contains a 13×5 cm opening through which the mouse can easily pass. The dark chamber has clear sides and a white floor. A fluorescent tube light (40 watt) placed above the chambers provides the only illumination. The Digiscan Animal Activity Monitor System RXYZCM16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolysis is seen as a general increase in exploratory activity in the lighted area. An increase in exploratory activity is relected by increased latency (the time for the mouse to move to the dark chamber when first placed in the center of the lighted area), increase in shuttle activity, increased or unaltered locomotor activity (number of grid lines crossed) and decreased time spent in the dark compartment.

Compounds of Formula I exhibit anxiolytic activity in this assay.

EXAMPLE 13

The Mouse Light/Dark Withdrawal Anxiety Test

The following procedure describes a method to determine whether compounds of Formula I effect the anxiety that occurs after abruptly ceasing chronic treatment with drugs of abuse.

Naive male BKW mice (25–30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 12). Anxiolysis is seen as a general increase in exploratory activity in the lighted area. An increase in exploratory activity is relected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with alcohol (8.0 % w/v in drinking water), nicotine (0.1 mg/kg, i.p., twice daily) or cocaine (1.0 mg/kg, i.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawal phase by intraperitoneal injection. Responses are represented as inhibition of the decrease in anxiolytic behavior after the alcohol, cocaine or nicotine treatment is ceased.

Intraperitoneal adminitration of compounds of Formula I decrease the anxiety associated with drug withdrawal in this model.

EXAMPLE 14

The Mouse Habituation/Cognitive Enhancement Test

The following describes a model to determine the cognitive enhancing effects of compounds of Formula I.

Young adult and aged BKW mice are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 12). Mice are exposed to the two-compartment test area over a 3 day period. The young mice habituate to the test area by day 3 and spend less time exploring the lighted area, whereas exploratory activity in the lighted area remains constant through day 3 for the aged mice. Exploratory activity is seen as latency (the time for the mouse to move to the dark chamber when first placed in the center of the lighted area), locomotor activity (number of grid lines crossed), number of rears and time spent in the lighted compartment. Vehicle or test compounds are administered to the aged mice by intraperitoneal injection. Cognitive enhancing effects in the aged rats are reflected by a decrease in exploratory activity by day 3.

Intraperitoneal adminitration of compounds of Formula I enhance cognition in this model.

We claim:

1. A compound of Formula I

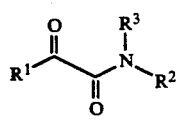

(I)

wherein $R^1$ is selected from

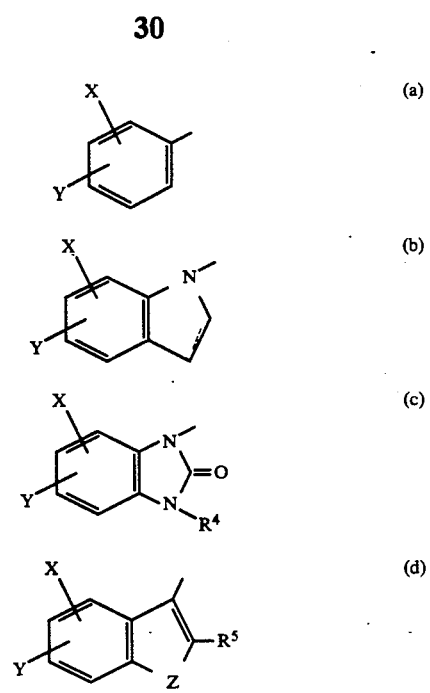

in which:
the dashed line denotes an optional bond;
X and Y are independently selected from hydrogen, halo, cyano, hydroxy, lower alkoxy, lower alkyl, nitro, amino, aminocarbonyl, (lower alkyl)amino, di(lower alkyl)amino, and (lower alkanoyl)amino;
Z is —O—, —S— or —N($R^4$)—; and
$R^4$ and $R^5$ are independently selected from hydrogen or lower alkyl or are together —(CH$_2$)$_n$— wherein n is an integer from 3 to 5; and
$R^2$ is selected from

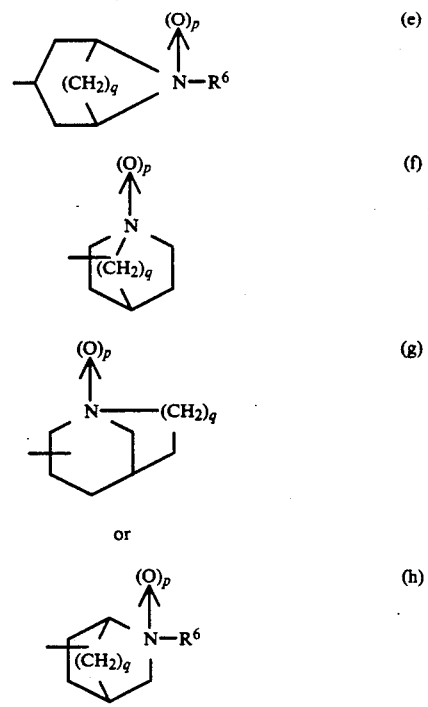

in which:
p is 0 or 1:

q is 1, 2 or 3; and

R[6] is $C_{1-7}$ alkyl, $C_{3-8}$ cycloalkyl, $C_{3-8}$ cycloalkyl-$C_{1-2}$ alkyl, or a group $(CH_2)_tR^7$ where t is 1 or 2 and R[7] is thienyl, pyrrolyl, or furyl, each optionally further substituted by one or two substituents selected from $C_{1-6}$ alkyl, $C_{1-6}$ alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally substituted by hydroxy, $C_{1-4}$ alkoxy, carboxy, esterified carboxy or in vivo hydrolyzable acyloxy; and R[3] is selected from hydrogen or lower alkyl; or a pharmaceutically acceptable salt, as an individual isomer or mixture of isomers thereof.

2. A compound of claim 1 in which R[3] is hydrogen, X and Y are independently selected from hydrogen and hydroxy, and p is 0.

3. A compound of claim 2 in which R[1] is Formula (d)

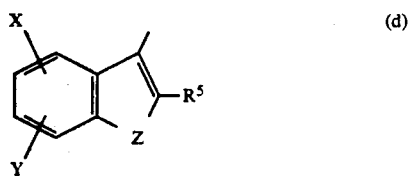

and R[2] is 1-azabicyclo[2.2.2]oct-3-yl or 1-azabicyclo[2.2.2]oct-4-yl.

4. A compound of claim 3 in which Z is —N(R[4])—.

5. A compound of claim 4 in which X, Y and R[5] are each hydrogen, R[4] is methyl, and R[2] is 1-azabicyclo[2.2.2]oct-3-yl, namely N-(1-azabicyclo[2.2.2]oct-3-yl)-1-methyl-α-oxo-3-indoleacetamide, or a pharmaceutically acceptable salt thereof.

6. The compound of claim 5 which is (S)-N-(1-azabicyclo[2.2.2]oct-3-yl)-1-methyl-α-oxo-3-indoleacetamide, or a pharmaceutically acceptable salt thereof.

7. The compound of claim 6 which is (S)-N-(1-azabicyclo[2.2.2]oct-3-yl)-1-methyl-α-oxo-3-indoleacetamide hydrochloride.

8. The compound of claim 5 which is (R)-N-(1-azabicyclo[2.2.2]oct-3-yl)-1-methyl-α-oxo-3-indoleacetamide, or a pharmaceutically acceptable salt thereof.

9. The compound of claim 8 which is (R)-N-(1-azabicyclo[2.2.2]oct-3-yl)-1-methyl-α-oxo-3-indoleacetamide hydrochloride.

10. A compound of claim 4 in which X, Y, R[4] and R[5] are each hydrogen, and R[2] is 1-azabicyclo[2.2.2]oct-3-yl namely, N-(1-azabicyclo[2.2.2]oct-3-yl)-α-oxo-3-indoleacetamide, or a pharmaceutically acceptable salt thereof.

11. The compound of claim 10 which is (S)-N-(1-azabicyclo[2.2.2]oct-3-yl)-α-oxo-3-indoleacetamide, or a pharmaceutically acceptable salt thereof.

12. The compound of claim 11 which is (S)-N-(1-azabicyclo[2.2.2]oct-3-yl)-α-oxo-3-indoleacetamide hydrochloride.

13. The compound of claim 10 which is (R)-N-(1-azabicyclo[2.2.2]oct-3-yl)-α-oxo-3-indoleacetamide, or a pharmaceutically acceptable salt thereof.

14. The compound of claim 13 which is (R)-N-(1-azabicyclo[2.2.2]oct-3-yl)-α-oxo-3-indoleacetamide hydrochloride.

15. The compound of claim 4 in which Y, R[4] and R[5] are each hydrogen, X is hydroxy in the 5-position, and R[2] is 1-azabicyclo[2.2.2]oct-3-yl namely N-(1-azabicyclo[2.2.2]oct-3-yl)-1-methyl-5-hydroxy-α-oxo-3-indoleacetamide, or a pharmaceutically acceptable salt thereof.

16. The compound of claim 15 which is (S)-N-(1-azabicyclo[2.2.2]oct-3-yl)-1-methyl-5-hydroxy-α-oxo-3-indoleacetamide, or a pharmaceutically acceptable salt thereof.

17. The compound of claim 16 which is (S)-N-(1-azabicyclo[2.2.2]oct-3-yl)-1-methyl-5-hydroxy-α-oxo-3-indoleacetamide hydrochloride.

18. The compound of claim 15 which is (R)-N-(1-azabicyclo[2.2.2]oct-3-yl)-1-methyl-5-hydroxy-α-oxo-3-indoleacetamide, or a pharmaceutically acceptable salt thereof.

19. The compound of claim 18 which is (R)-N-(1-azabicyclo[2.2.2]oct-3-yl)-1-methyl-5-hydroxy-α-oxo-3-indoleacetamide hydrochloride.

20. A compound of claim 4 in which X, Y and R[5] are each hydrogen, R[4] is methyl, and R[2] is 1-azabicyclo[2.2.2]oct-4-yl namely N-(1-azabicyclo[2.2.2]oct-4-yl)-1-methyl-α-oxo-3-indoleacetamide, or a pharmaceutically acceptable salt thereof.

21. The compound of claim 20 which is (1-azabicyclo[2.2.2]oct-4-yl)-1-methyl-α-oxo-3-indoleacetamide hydrochloride.

22. A compound of claim 4 in which X and Y are each hydrogen, R[4] and R[5] together are —(CH$_2$)$_4$—, and R[2] is 1-azabicyclo[2.2.2]oct-3-yl, namely N-(1-azabicyclo[2.2.2]oct-3-yl)-1,2,3,4-tetrahydro-α-oxo-10-pyrido[1,2-a]indoleacetamide, or a pharmaceutically acceptable salt thereof.

23. A compound of claim 3 in which Z is —S—.

24. A compound of claim 23 in which X, Y and R[5] are each hydrogen and R[2] is 1-azabicyclo[2.2.2]oct-3-yl namely, N-(1-azabicyclo[2.2.2]oct-3-yl)-α-oxo-3-benzothiopheneacetamide, or a pharmaceutically acceptable salt thereof.

25. A compound of claim 3 in which Z is —O—.

26. A compound of claim 25 in which X, Y and R[5] are each hydrogen and R[2] is 1-azabicyclo[2.2.2]oct-3-yl namely, N-(1-azabicyclo[2.2.2]oct-3-yl)-α-oxo-3-benzofuranacetamide, or a pharmaceutically acceptable salt thereof.

27. A compound of claim 2 in which R[1] is Formula (a)

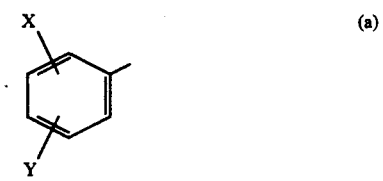

in which R[2] is 1-azabicyclo[2.2.2]oct-3-yl or 1-azabicyclo[2.2 2]oct-4-yl.

28. A compound of claim 27 in which X and Y are each hydrogen and R[2] is 1-azabicyclo[2.2.2]oct-3-yl namely, N-(1-azabicyclo[2.2.2]oct-3-yl)-α-oxo-benzeneacetamide, or a pharmaceutically acceptable salt thereof.

29. A compound of claim 2 in which R¹ is Formula (b)

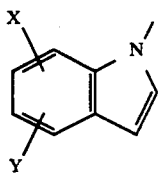

in which R² is 1-azabicyclo[2.2.2]oct-3-yl or 1-azabicyclo[2.2.2]oct-4-yl.

30. A compound of claim 29 in which the optional bond is present, X and Y are each hydrogen and R² is 1-azabicyclo[2.2.2]oct-3-yl namely, N-(1-azabicyclo[2.2.2]oct-3-yl)-α-oxo-1-indoleacetamide, or a pharmaceutically acceptable salt thereof.

31. A compound of claim 29 in which the optional bond is absent, X and Y are each hydrogen and R² is 1-azabicyclo[2.2.2]oct-3-yl namely, N-(1-azabicyclo[2.2.2]oct-3-yl)-2,3-dihydro-α-oxo-1-indole acetamide, or a pharmaceutically acceptable salt thereof.

32. A compound of claim 2 in which R¹ is Formula (c)

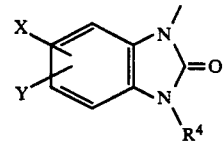

in which R² is 1-azabicyclo[2.2.2]oct-3-yl or 1-azabicyclo[2.2.2]oct-4-yl.

33. A compound of claim 32 in which X, Y and R⁴ are each hydrogen and R² is 1-azabicyclo[2.2.2]oct-3-yl namely, N-(1-azabicyclo[2.2.2]oct-3-yl)-α-oxo-1-benzimidazolidinoneacetamide, or a pharmaceutically acceptable salt thereof.

34. A pharmaceutical composition comprising a therapeutically effective amount of a compound of claim 1 in combination with a pharmaceutically acceptable excipient.

* * * * *